United States Patent [19]
Lorenzi et al.

[11] Patent Number: 4,502,253
[45] Date of Patent: Mar. 5, 1985

[54] SURFACE TREATING AND TESTING APPARATUS

[75] Inventors: Donald E. Lorenzi; Helmut F. Wagerer, both of Des Plaines, Ill.

[73] Assignee: Magnaflux Corporation, Chicago, Ill.

[21] Appl. No.: 407,656

[22] Filed: Aug. 12, 1982

[51] Int. Cl.³ .............................................. B24B 49/10
[52] U.S. Cl. .................................. 51/165 R; 51/34 R; 51/35; 51/45; 51/165.92
[58] Field of Search ................. 51/34 E, 34 R, 35, 45, 51/134.5 R, 165 R, 165.72, 165.73, 165.92

[56] References Cited

U.S. PATENT DOCUMENTS

| | | | |
|---|---|---|---|
| 2,947,121 | 8/1960 | Coes | 51/134.5 R |
| 3,495,166 | 2/1970 | Lorenzi | 324/37 |
| 3,827,190 | 8/1974 | Moriguchi | 51/165.92 |
| 3,953,943 | 5/1976 | Nakaoka | 51/165.92 |
| 3,978,624 | 9/1976 | Merkel | 51/165.92 |
| 4,027,982 | 6/1977 | Obishi | 356/237 |
| 4,199,902 | 4/1980 | Sauerland | 51/165 R |

FOREIGN PATENT DOCUMENTS

| | | | |
|---|---|---|---|
| 2523375 | 12/1976 | Fed. Rep. of Germany | 51/165.72 |
| 2465564 | 3/1981 | France | |
| WO80/02667 | 12/1980 | PCT Int'l Appl. | 51/165 R |
| 509416 | 4/1976 | U.S.S.R. | 51/165.73 |

Primary Examiner—Harold D. Whitehead
Attorney, Agent, or Firm—Neuman, Williams, Anderson & Olson

[57] ABSTRACT

Apparatus for grinding and simultaneously testing steel billets or other parts to remove portions which contain defects. The defects are detected by a probe which engages the part at a point in proximity to the portion engaged by a grinding wheel. Preferably, the probe is carried in an opening provided in the surface of the grinding wheel and is electrically connected through a rotary coupling device to indicating apparatus. A probe may be a magnetic probe, either an eddy current or leakage field probe, or may include means for detecting light or other radiant energy reflected from the surface of the part. The apparatus is adaptable for the automatic control of the grinding operation.

12 Claims, 5 Drawing Figures

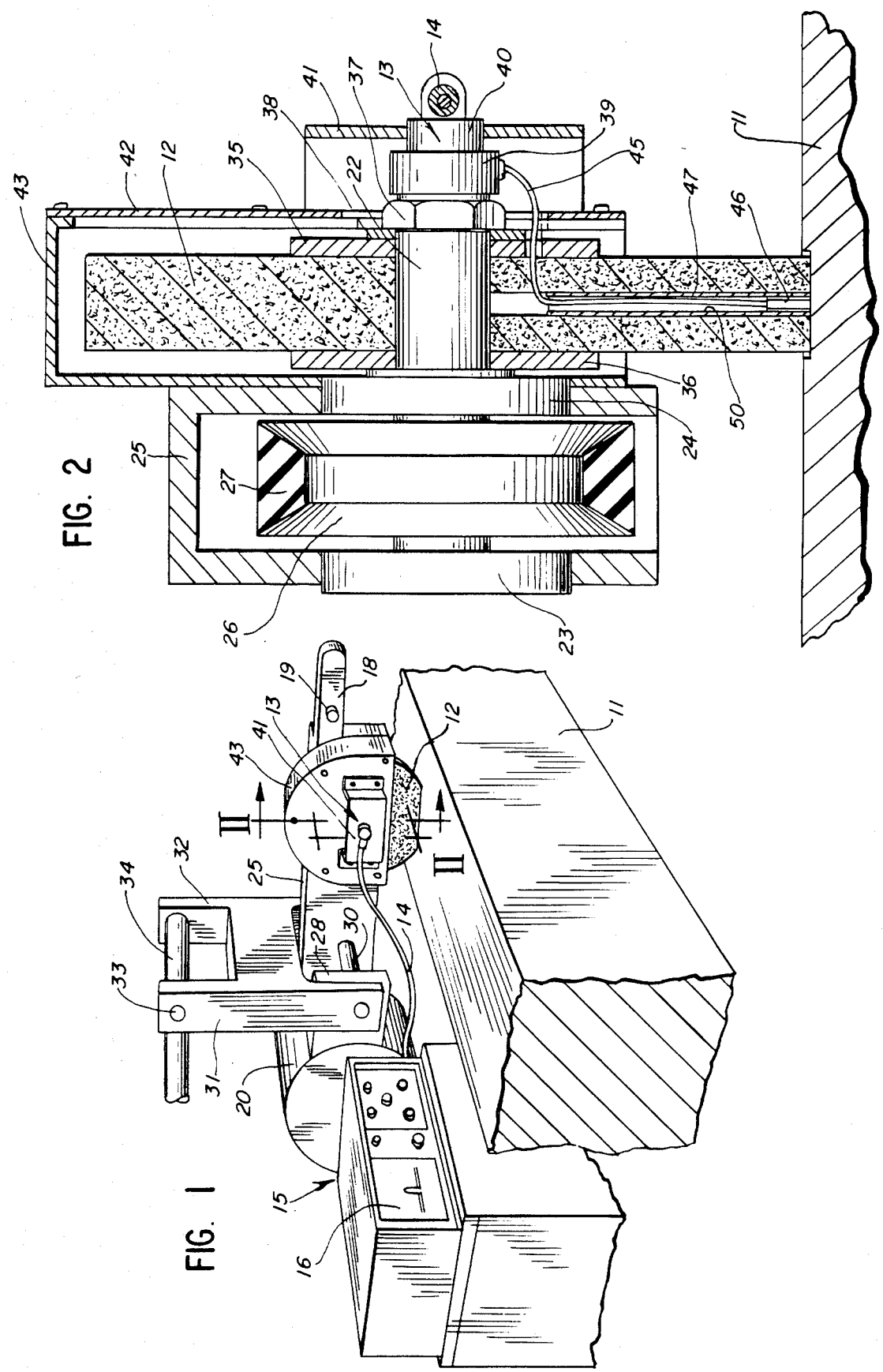

SURFACE TREATING AND TESTING APPARATUS

This invention relates to surface treating and testing apparatus and more particularly to apparatus which performs a surface treating operation while also performing a testing operation in a manner such as to greatly reduce operating time, errors and waste of material and to otherwise increase productivity and efficiency. The apparatus is relatively simple in construction and operation, is easy to use and is highly reliable while being economically manufacturable.

BACKGROUND OF THE INVENTION

Non-destructive testing procedures have heretofore been used in conjunction with the processing of metal parts or the like to detect defective parts, to avoid unnecessary and expensive processing of defective parts and to otherwise obtain very important advantages. In the processing of steel billets, for example, the magnetic particle inspection method has been used to detect defects prior to the performance of expensive subsequent processing operations on the billet. With the magnetic particle inspection method, finely divided particles, usually in a liquid carrier, are applied over the surface of the billet during or after magnetization of the billet, the particles being concentrated over any leakage fields produced by surface or subsurface cracks or defects. When cracks are indicated by the magnetic particle inspection, the affected portion of the billet is ground away so that the billet is free of the defect in subsequent processing operations.

Although highly advantageous, such procedures still leave something to be desired in that the grinding operation must be carefully performed and it takes a substantial length of time for an operator to process a billet which has a considerable number of indicated defects.

SUMMARY OF THE INVENTION

This invention was evolved with the general object of improving upon prior art procedures and more particularly with respect to reducing the time required in performing the procedures, minimizing waste of material and eliminating errors.

In accordance with the invention, apparatus is provided for grinding and simultaneously testing a steel billet to remove portions of the billet which contain surface and sub-surface cracks or other defects while minimizing the removal of portions of the billet which do not contain such defects. It will be understood that although illustrated herein as applied to apparatus for grinding steel billets, the principles of the invention may be applied to other types of surface treating operations and on types of parts other than steel billets.

In accordance with an important feature of the invention, a non-destructive testing probe is moved into proximity to the surface of a part being ground or otherwise treated, the probe being preferably supported with the grinding wheel or other surface treating member for movement therewith, relative to the part being treated. In an apparatus for testing steel billets, the probe is preferably supported within a radially extending passage of a grinding wheel, the end of the probe being flush with the peripheral surface of the grinding wheel. With this arrangement, the characteristics of the surface of the billet being ground may be tested during the grinding operation and with suitable indicating apparatus, any cracks in the billet may be indicated so that the operator is able to continue grinding only so long as the grinding wheel is grinding a portion of the part which has a crack therein.

In one embodiment, the probe is an electromagnetic probe, preferably an eddy current probe. To couple the probe to indicating means, a slip-ring unit is provided on the support shaft for the grinding wheel.

In another embodiment, the probe is operative to transmit light toward the surface of the part and to receive reflected light therefrom, the amount of reflected light being detected to indicate any surface crack in the part. Preferably, a light guide is provided, a portion of which is disposed in a radially extending passage of the grinding wheel, one end of the light guide being positioned at the peripheral surface of the wheel and the other end being positioned on the axis of rotation of the billet. A light source, preferably a laser, is arranged to impinge a narrow light beam on the end of the light guide and means are provided for receiving and detecting the light reflected from the surface of the billet and transmitted back through the light guide.

A further feature of the invention is that the probe in each embodiment may remain operative while the surface of the grinding wheel wears away during the grinding operation. In the embodiment using a light guide, the end of the guide simply wears away as the surface of the grinding wheel wears away, to always be flush with the surface of the grinding wheel.

In the embodiment using an electromagnetic probe, the probe is retracted as the surface of the wheel wears away. A specific feature relates to the support of the probe through an arrangement which permits it to move radially inwardly while preventing outward movement thereof. In a very simple but highly effective construction, bristles are provided which engage serrations to allow movement radially inwardly while preventing movement radially outwardly.

Additional important features of the invention relate to the details of construction and mounting of the electromagnetic probe and to the circuitry and structure for energization of the probe and transmission and processing of signals therefrom.

Additional features relate to details of construction of the embodiment using a light guide, operative to obtain a high sensitivity to cracks while also obtaining a high degree of reliability.

This invention contemplates other objects, features and advantages which will become more fully apparent from the following detailed description taken in conjunction with the accompanying drawings.

BRIEF DESCRIPTION OF THE DRAWINGS

FIG. 1 is a perspective view illustrating apparatus for grinding and simultaneously testing a steel billet and using an electromagnetic probe;

FIG. 2 is a sectional view taken substantially along line II—II of FIG. 1 and illustrating the mounting of a probe and associated slip-ring structure in association with a grinding wheel;

DESCRIPTION OF A PREFERRED EMBODIMENT

Figure 4:
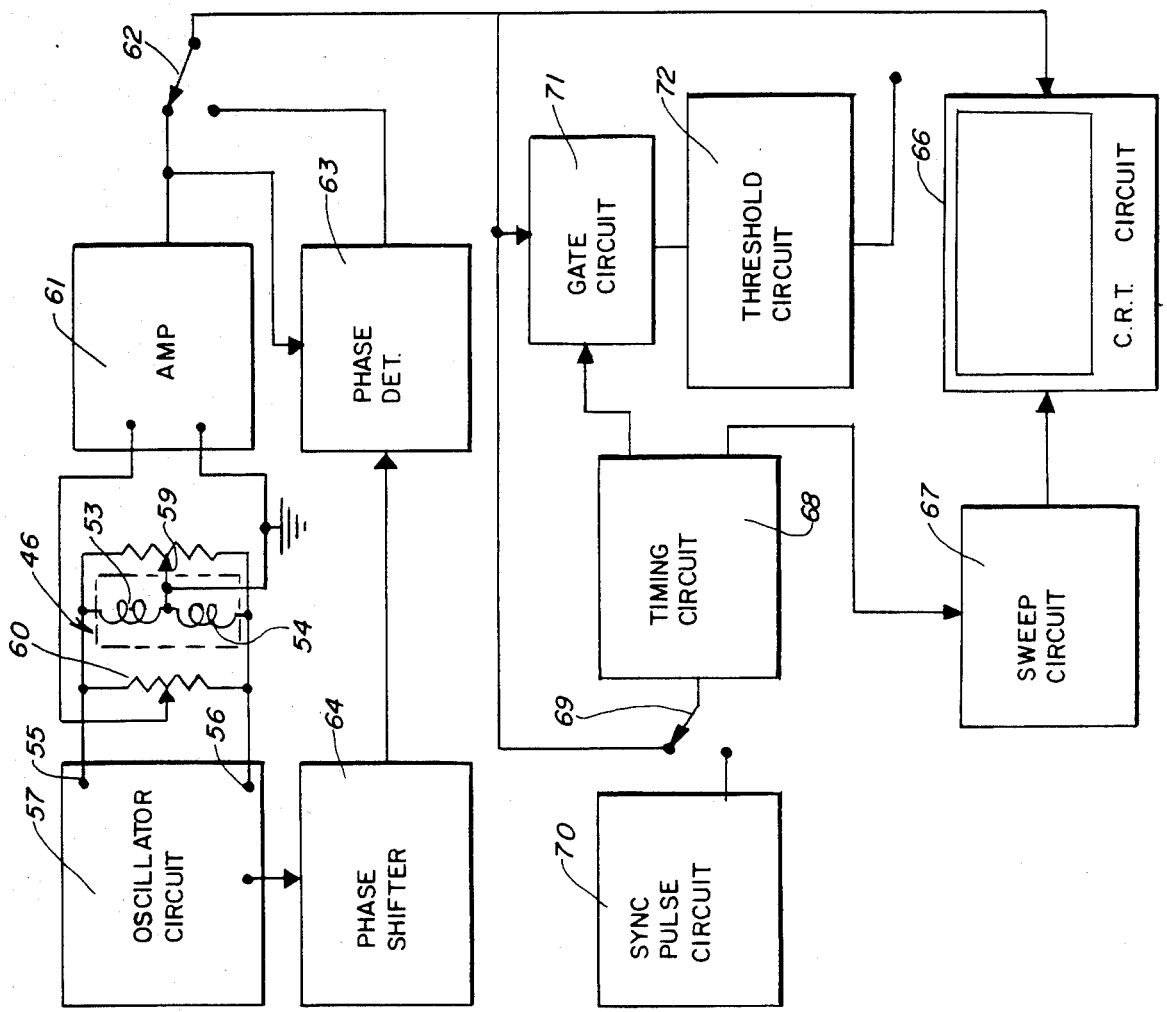
FIG. 4 is a schematic electrical diagram illustrating circuitry for the apparatus of FIGS. 1–3, using an eddy current probe of a crossed coil type.

Reference numeral 10 generally designates a grinding and testing apparatus constructed in accordance with the principles of this invention, shown in use in grinding and simultaneously testing a steel billet 11. The illustrated apparatus includes a grinding wheel 12 shown with its periphery in engagement with the upper surface of the billet 11. The grinding wheel 12 carries an eddy current probe which moves in proximity to the surface of the billet 11 during each revolution of the wheel 12. The probe is connected through a slip ring unit 13 and a cable 14 to an instrument 15 which includes a cathode ray tube display 16 and suitable controls. It will be understood that coupling devices other than a slip ring unit may be used including, for example, an electromagnetic rotary coupling device.

The apparatus 10 is usable, for example, in removing portions of the billet 11 where marks have previously been applied to indicate the location of surface and subsurface cracks or other defects. The operator, using a control handle 18 and a control button 19 energizes an electric motor 20 to rotate the wheel 12 and then moves the wheel 12 into engagement with the billet 11, in a position as illustrated, while looking for a crack indication on the display 16 and/or listening for an audible crack indication which may also be produced by the instrument 15.

When a crack indication is observed or heard, the operator may continue grinding, stopping when the crack indication disappears. Then billet-handling apparatus (not shown) may be operated to move the billet relative to the grinder and to position another defect-indicating mark opposite the wheel 12. Such billet-handling apparatus may desirably include means for moving the billet 11 longitudinally and may also function to rotate the billet about its axis.

With the apparatus 10, a crack or defect may be indicated with a high degree of accuracy and reliability and only the defective portion of the billet is removed. Each grinding operation can be quickly performed so that the operator may move on to the next marked region of the billet 11.

The defect-indicating marks may be applied, for example, through a magnetic particle inspection procedure in which finely divided magnetic particles, usually in a liquid carrier, are applied over the surface of the billet 11 to be concentrated over any surface and subsurface cracks or defects which create leakage fields. The part may be magnetized during the application of the particles or may be magnetized prior to the application thereof, to leave a residual field. The marks may be provided by the concentrations of magnetic particles and may be augmented by applying paint or the like thus clearly indicating the position of a defective region of the part.

The grinding wheel 12 may be supported and driven by any suitable arrangement and, in some applications, it may be desirable to rotate the grinding wheel 12 about a stationary axis while moving the part to a position in which it is engaged by the wheel 12. In the illustrated arrangement, the grinding wheel 12 is supported on a shaft 22 which is journalled by bearings 23 and 24 carried by a housing 25. A pulley 26 on the shaft 22 is coupled through a belt 27 to a pulley (not shown) on the shaft of the motor 20. The motor 20 serves as a counterbalance and is secured to the housing 25 and to an arm 28 which are pivotal on a horizontal shaft 30. Shaft 30 extends between the lower ends of a pair of rigidly connected arms 31 and 32, the upper ends of which are pivotally supported on a horizontal shaft 33 carried by a fixed support 34. With this type of arrangement, the operator may move the grinding wheel 12 vertically as well as horizontally, in a direction transverse to the longitudinal axis of the billet 11, to position the wheel 12, as desired. Relative movement in a longitudinal direction may be controlled by moving the billet 11. It will be understood that the invention is not limited to any particular support and drive arrangement for the billet and, although specific features of the invention relate to the mounting of a testing probe in a grinding wheel, the invention can be applied to other types of surface treating operations including operations in which a surface treating member is not rotatable.

The grinding wheel 12 is mounted on the shaft 22 between a pair of flanges 35 and 36 and is held in place by a nut 37 threaded on the end of the shaft 22, with a washer 38 being disposed between the nut 37 and the flange 36. The slip ring unit 13 includes a rotatable part 39 threaded or otherwise secured on the end of the shaft 22 and a stationary part 40 which is connected to the end of the cable 14 and which is connected to a bracket 41 on an end plate 42 of a shroud 43 for the grinding wheel 12. Electrical contacts within the rotatable part 39 of the slip ring unit 13 are connected through a cable 45 to an eddy current probe 46 which is mounted in the outer end of a radially extending passage 47 formed in the grinding wheel 12.

Figure 3:
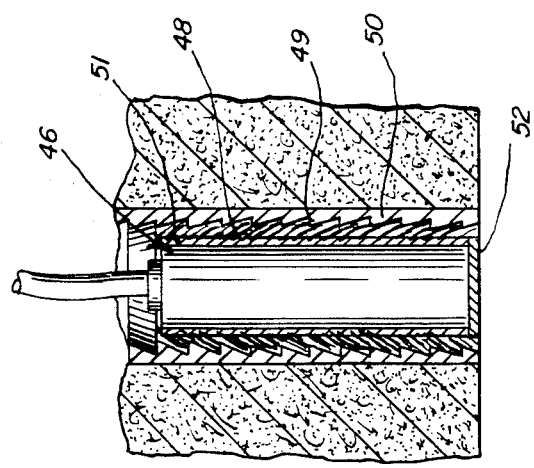
FIG. 3 is a sectional view, on an enlarged scale, illustrating details of mounting of the probe in the grinding wheel.

An important specific feature relates to the mounting of the probe 46 in a manner such as to adjust for wear of the periphery of the grinding wheel 12 during operation. In the illustrated arrangement, the probe 46 is initially positioned with its terminal end in flush alignment with the outer peripheral surface of the grinding wheel 12 but means are provided to permit movement radially inwardly when the periphery of the grinding wheel 12 wears, so as to maintain the terminal end of the probe 46 in flush alignment with the outer peripheral surface of the wheel 12. As illustrated in FIG. 3, bristles 48 are secured to the probe 46 and extend radially away from the axis of the probe 46 as well as radially outwardly with respect to the axis of the grinding wheel 12. The bristles 48 engage serrations 49 formed on the inner surface of a sleeve 50 which is disposed within the passage 47. Sleeve 50 preferably has a thin wall and is of a material such as brass or aluminum which will readily wear away as the periphery of the grinding wheel 12 wears away. The bristles 48 allow the probe to be moved radially inwardly but engage the serrations 49 to prevent outward movement of the probe 46 in response to centrifugal force.

The provision of the sleeve 50 is highly advantageous in most applications but in others it may not be necessary and the bristles 48 may directly engage the inside surface of the passage 47 which, being formed in a grinding wheel, is inherently a rough surface providing a high degree of friction. It is also possible to form the sleeve 50 by coating the inside surface of the passage 47 with a suitable hardenable plastic material, such as an epoxy, and then forming, if necessary, serrations or grooves therein. It should also be understood that the probe may be actively retracted by providing a servomechanism. Other types of probes may be used. For example, the probe 46 may be supported on an arm attached to the side of the wheel 12.

As shown in the enlarged detail view of FIG. 3, the bristles 48 may preferably be secured to a sleeve 51 on the outside of the probe 46 and a thin wear member 52 may be secured to the outer terminal end of the probe 46 for protecting the probe during operation. The probe 46, by way of example, may be an eddy current probe of a crossed coil type, with a construction and operation as disclosed in U.S. Pat. No. 3,495,166. However, other types of eddy current probes may be used, including probes using only one coil, and it is also possible to use other types of magnetic probes, particularly probes of the type operative to detect leakage fields.

FIG. 4 is a schematic diagram illustrating a circuit usable with a probe of the crossed coil type. A pair of coils 53 and 54 of the probe 46 are connected in series and to output terminals 55 and 56 of an oscillator 57 which may include an output driver stage with an output transformer having a secondary winding connected to the terminals 55 and 56. A pair of balance potentiometers 59 and 60 are provided which are connected to the terminals 55 and 56, the movable contact of the potentiometer 59 being connected to the junction between the coils 53 and 54 and being connected to ground. The movable contact of the potentiometer 60 is connected to one input of an amplifier 61 having a second input terminal connected to ground. The output of the amplifier 61 is connectable through a selector switch 62 to indicating circuitry and is also connected to one input of a phase detector 63 which has a second input connected to the output of a phase shifter 64 which is connected to the oscillator circuit. In a second position of the selector switch 62, the output of the phase detector 63 is connected to the indicating circuitry.

In the illustrated arrangement, the indicating circuitry includes a cathode ray tube circuit 66 which has a vertical input connected to the selector switch 62. A horizontal input of the circuit 66 is connected to the output of a sweep circuit 67 which receives a signal from a timing circuit 68. The timing circuit 68 has an input connectable through a selector switch contact 69 to the selector switch 62, permitting synchronization of the timing circuit with signals detected by the probe.

Alternatively, the input of the timing circuit 68 is connected through the selector switch contact 69 to a synchronizing pulse circuit 70 which may, for example, respond to a signal pulse developed at a certain angular position of the grinding wheel 12, during each rotation thereof. The output of the probe circuitry, at the selector switch 62, may also be connected through a gate circuit 71 and a threshold circuit 72 to an indicating circuit 73 which may, for example, energize an audible signal device. The gate circuit 71 is connected to the timing circuit 68 and may be so controlled as to be operative only during movement of the probe 46 past the engaged portion of the billet 11. The threshold circuit 72 may be adjusted to develop an output signal only when the detected signal is above a certain amplitude.

Non-destructive testing probes other than electromagnetic probes may be used to detect flaws in the surface of a part being ground or otherwise subjected to a surface treating operation.

Figure 5:
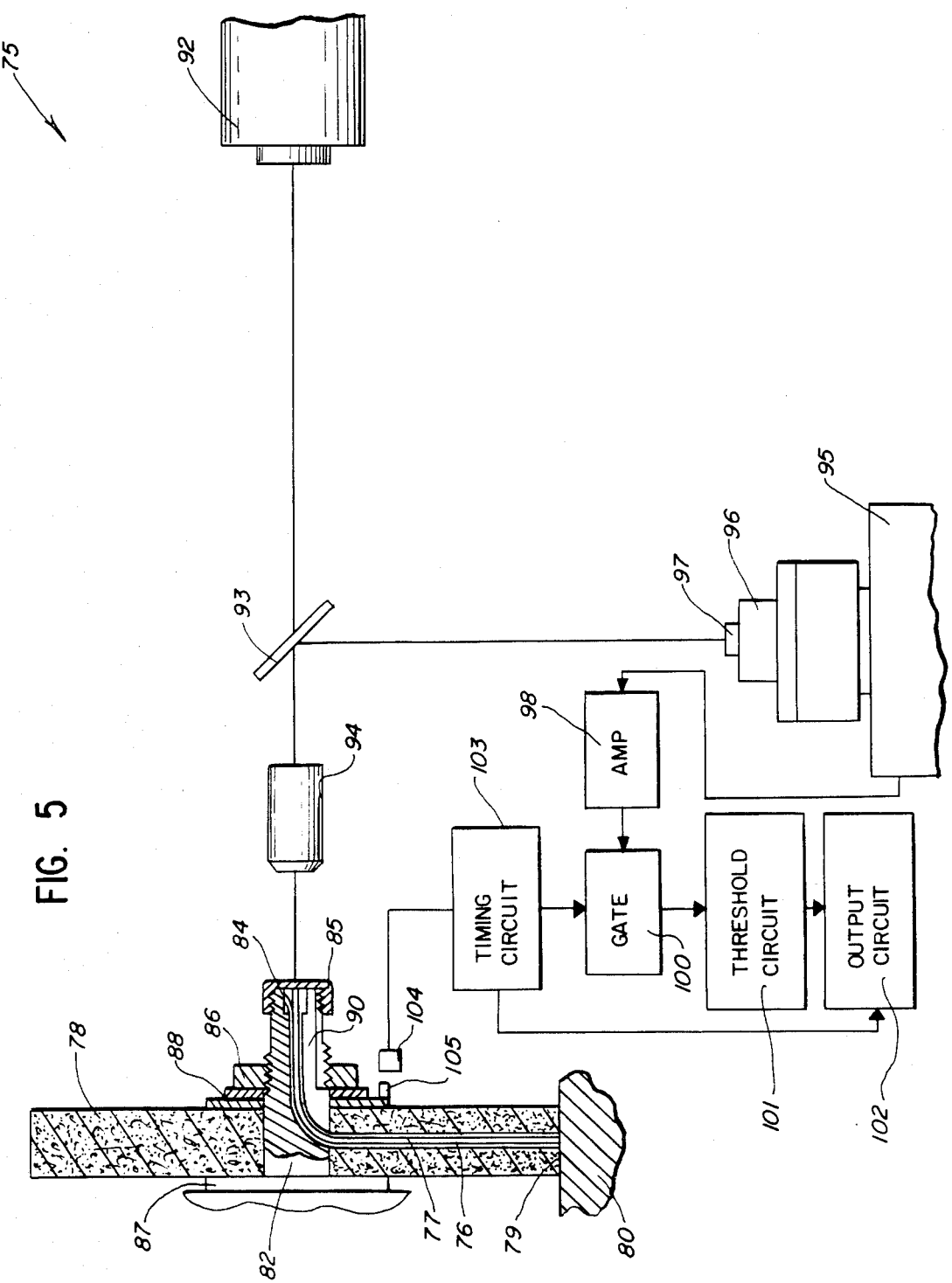
FIG. 5 is a view illustrating a system for grinding of a part while optically detecting flaws in the surface of the part.

FIG. 5 illustrates a system for optical detection of flaws, generally designated by reference numeral 75 in the system 75, a plastic fiber light guide 76 is disposed in a passage 77 in a grinding wheel 78 with a terminal end of the guide 76 being flush with the peripheral surface of the grinding wheel 78, to move into proximity to a surface 79 of a part 80 during each rotation of the wheel 78. The light guide 76 extends through a slot 81 in a shaft 82 on which the grinding wheel 78 is mounted and an opposite terminal end of the guide 76 projects through a centering disk 84 which is held on the end of the shaft 82 by a holder 85 threaded on the end of the shaft 82. A nut 86 is threaded on the shaft 82 to hold the wheel 78 between flanges 87 and 88, a washer 89 being disposed between nut 86 and flange 88. A fitting 90 may be diposed in the slot 86 to hold the light guide 76 in place, the fitting 90 and the slot 81 having spaced facing arcuate surfaces together defining a passage for receiving the guide 76.

A laser 92 is positioned to project a beam along the axis of rotation of the grinding wheel 78 and through a beam splitter 93 and a lens 94 to impinge on the terminal end of the guide 76 which is on the axis of the grinding wheel 78. The light from the laser 92 is transmitted through the guide 76 to the surface 79 to be reflected therefrom and back through the light guide 76 and through the lens 96 to impinge on a reflective surface of the beam splitter 93. The light reflected from the beam splitter 93 is received by a photomultiplier 95 which includes a fitting 96 defining an entrance window through which light may be received and measured. An optical bandpass filter 97 is secured to the fitting 96.

The beam splitter 93 functions to allow transmission of light from the laser 92 to the end of the light guide 76 and to transmit reflected light to the photomultiplier 95, while blocking transmission of light directly from the laser and from the beam splitter 93 to the photomultiplier 95. The beam splitter may be of a conventional type or may be in the form of a mirror having a very small central aperture through which the laser beam is projected, it being noted that the reflected light is dispersed through a substantial angle of divergence.

The lens 94 serves to focus the laser beam on the end of the light guide 76 but more importantly, it serves to collect the reflected light and to transmit the collected transmitted light to the beam splitter and thence to the photomultiplier 95. As a result, the arrangement is highly sensitive to variations in the light reflected from the surface 79.

By way of example and not by way of limitation, the light guide 76 may be a plastic fiber having a diameter of 0.036 inches. The lens 94 is a 5× microscope objective with a NA of 0.1, the lens 94 being effective to magnify the reflected light from 0.036 inches at the end of the guide 76 to 0.180 inches at the window of the photomultiplier 95. It is possible to provide a lens between the beam splitter 93 and the photomultiplier 95, rather than between the beam splitter 93 and the light guide end but the arrangement as shown has the advantage that it is more efficient in transmitting a wide cone at the light guide end into a narrow cone at the photomultiplier window.

The filter 97 serves to improve the signal to noise ratio, especially with respect to limiting interference from room lights. By way of example, a filter may be used having a center wavelength of 6328 Angstroms and a band width of on the order of 80 to 160 Angstroms.

The output of the photomultiplier 95 is applied through an amplifier 98, a low pass filter 99, a gate circuit 100 and a threshold circuit 101 to an output circuit 102. The gate circuit 100 is controlled from a timing circuit 103 which is connected to a reed switch 104 adjacent the path of movement of a magnet 105 carried by the support flange 88 for the grinding wheel 78. The timing circuit 103 may also control the output circuit 102 which may include a CRT or other visible display device.

Although not shown in FIG. 5, it will be understood that means are provided for supporting the optical components in accurate relationship to the axis of rotation of the grinding wheel 78. All of the optical components as well as the bearings for the support shaft 82 should be securely mounted on a common support. In some applications, it may be desirable to mount all of such components on a stationary support and move the part to be treated into cooperative relationship to the grinding wheel 78 or other surface treating member.

The system of FIG. 5 is capable of detecting relatively narrow grooves or other defects in the surface of a part. It has a potential disadvantage in connection with a billet-grinding operation in which relatively coarse particles of a grinding wheel may become positioned opposite the end of the light guide 76 to block transmission of light. In other grinding operations or for polishing or other surface-treating operations, it may be used to advantage.

It will be understood that modifications and variations may be effected without departing from the spirit and scope of the novel concepts of this invention.

We claim:

1. In grinding apparatus, rotatable grinding wheel means having a cylindrical peripheral surface for abrasive engagement with a surface portion of a part, and probe means within said wheel means and having a sensing surface flush with said cylindrical peripheral surface and intermediate the opposite axial ends thereof, and sensing surface being slidably engaged with said surface portion of the part during a portion of each complete rotation of said grinding wheel means, and means connected to said probe means arranged to develop an output signal of one form while sliding over a homogeneous part surface portion and of a substantially different form while sliding over a part surface portion having a crack therein.

2. In apparatus as defined in claim 1, said probe means being arranged to maintain said sensing surface in flush relation to said cylindrical peripheral surface while said cylindrical peripheral surface is worn down to a smaller diameter during grinding operation.

3. In apparatus as defined in claim 2, said probe means including a wear resistant member defining said sensing surface.

4. In apparatus as defined in claim 1, said probe means being a magnetic probe operative to develop an electrical output signal of one form while sliding over a homogeneous part surface portion and of a substantially different form while sliding over a part surface portion having a crack therein.

5. In apparatus as defined in claim 4, said probe means including an eddy current probe.

6. In apparatus as defined in claim 2, said probe means including support means defining a opening extending radially inwardly form from an outer end flush with said cylindrical peripheral surface, and a probe supported in said opening and having a sensing end at said outer end thereof, said probe being movable radially inwardly with said opening.

7. In apparatus as defined in claim 6, said probe means including bristle means acting between the outside of said probe and the inside of said opening to prevent movement of said probe radially outwardly while allowing movement of said probe radially inwardly.

8. In apparatus as defined in claim 7, said probe means including serrations engageable by said bristle means.

9. In apparatus as defined in claim 1, said probe and connecting means including light guide means extending radially inwardly from an outer terminal end forming said sensing surface to an opposite inner terminal end, means for transmitting light into said inner terminal end to be transmitted through said light guide means to said part surface portion, and means for detecting light transmitted from said inner terminal end after reflection from said part surface portion and transmission through said light guide means to said inner terminal end.

10. In apparatus as defined in claim 9, beam splitter means for separation of light transmitted to and received from said inner terminal end of said light guide means.

11. In apparatus as defined in claim 10, lens means between said beam-splitter means and said light guide means.

12. In apparatus as defined in claim 9, said light guide means being arranged to wear away while said cylindrical peripheral surface is worn down to a smaller diameter during grinding operation.

* * * * *